United States Patent [19]

Halm et al.

[11] Patent Number: 4,762,940

[45] Date of Patent: Aug. 9, 1988

[54] METHOD FOR PREPARATION OF ALKYLHALOSILANES

[75] Inventors: Roland L. Halm, Madison, Ind.; Andrew B. Pierce, Louisville, Ky.; Oliver K. Wilding, Jr., Sully, Wales

[73] Assignee: Dow Corning Corporation, Midland, Mich.

[21] Appl. No.: 132,444

[22] Filed: Dec. 11, 1987

[51] Int. Cl.$^4$ ............................ C07F 7/16; B01J 23/72
[52] U.S. Cl. ............................... 556/472; 252/183.13; 252/186.24
[58] Field of Search ............. 556/472; 252/182, 186.24

[56] References Cited

U.S. PATENT DOCUMENTS

| | | | |
|---|---|---|---|
| 2,380,995 | 8/1945 | Rochow | 260/607 |
| 2,380,996 | 8/1945 | Rochow et al. | 260/607 |
| 2,380,997 | 8/1945 | Patnode | 252/225 |
| 2,383,818 | 8/1945 | Rochow et al. | 260/607 |
| 2,443,902 | 6/1948 | Ferguson et al. | 260/448.2 |
| 2,464,033 | 3/1949 | Gilliam | 260/448.2 |
| 2,666,775 | 1/1954 | Nitzsche | 260/448.2 |
| 3,069,452 | 12/1962 | Rossmy | 260/448.2 |
| 3,133,109 | 5/1964 | Dotson | 260/448.2 |
| 3,446,829 | 5/1969 | Zock | 260/448.2 |
| 4,218,387 | 8/1980 | Maas et al. | 556/412 |
| 4,281,149 | 7/1981 | Shade | 556/472 |
| 4,307,242 | 12/1981 | Shah et al. | 556/472 |
| 4,314,908 | 2/1982 | Downing et al. | 556/472 X |
| 4,487,950 | 12/1984 | Ward, III et al. | 556/472 |
| 4,500,724 | 2/1985 | Ward, III et al. | 556/472 |
| 4,503,165 | 3/1985 | Hashiguchi et al. | 502/225 |
| 4,504,596 | 3/1985 | Schoepe et al. | 502/225 |
| 4,602,101 | 7/1986 | Halm et al. | 556/472 |
| 4,645,851 | 2/1987 | Prud'Homme | 556/472 |
| 4,656,301 | 4/1987 | Prud'Homme et al. | 556/472 |
| 4,661,613 | 4/1987 | Prud'Homme et al. | 556/472 |

FOREIGN PATENT DOCUMENTS

| | | | |
|---|---|---|---|
| 0028009A2 | 6/1981 | European Pat. Off. | 556/472 UX |
| 0138678A2 | 4/1985 | European Pat. Off. | 556/472 UX |
| 0138679A2 | 4/1985 | European Pat. Off. | 556/472 UX |
| 0191502A2 | 8/1986 | European Pat. Off. | 556/472 UX |
| 0194214 | 9/1986 | European Pat. Off. | 556/472 UX |
| 1165026 | 3/1964 | Fed. Rep. of Germany | 556/472 UX |
| 2153697A | 8/1985 | United Kingdom | 556/472 UX |
| 0150513 | 6/1959 | U.S.S.R. | 556/472 |
| 151336 | 10/1982 | U.S.S.R. | 556/472 UX |

OTHER PUBLICATIONS

Lobusevich et al., *Zhurnal Obshchei Khimii*, (Aug. 1964), 34:8, pp. 2727-2729.

*Primary Examiner*—Paul F. Shaver
*Attorney, Agent, or Firm*—Carl A. Yorimoto

[57] ABSTRACT

What is disclosed is a method for controlling a process for the preparation of alkylhalosilanes from silicon and alkyl halides where metal arsenides and alloys of arsenic are used as promoters to enhance selectivity, overall yields of usable silanes, and silicon utilization. Also, disclosed is a composition comprising a direct reaction silicon/copper contact mass which includes arsenic as a component.

19 Claims, No Drawings

METHOD FOR PREPARATION OF ALKYLHALOSILANES

BACKGROUND INFORMATION

This invention relates to a method for preparing alkylhalosilanes. More specifically, this invention relates to the use of arsenic compounds and arsenic alloys as a replacement for tin as a catalyst in the direct reaction of silicon and an alkyl halide to produce alkylhalosilanes. The benefits to be derived from using the instant invention are increased alkylhalosilane yields, selectivity of certain alkylhalosilanes over other, less preferred alkylhalosilanes, and overall higher utilization of raw materials in the reaction Halosilanes and organohalosilanes are well known reactive chemical intermediates used extensively in the semiconductor and silicones industries, respectively. Halosilanes and organohalosilanes are produced primarily by the direct reaction of silicon with the corresponding hydrogen halide or organic halide. Hereafter in this application the term "the direct reaction" will refer either to the reaction of silicon with a hydrogen halide or the reaction of silicon with an organic halide. The direct reaction to form the halosilanes has been known since the work of Buff and Wohler in 1857 and Combes in 1896. The direct reaction to form organohalosilanes was first disclosed by Rochow and his co-workers, beginning in the mid-1940'". The direct reaction for producing alkylhalosilanes is well-known and has been refined and modified in many ways since the early work of Rochow.

It should be noted that the direct reaction for producing alkylhalosilanes produces a distribution of silanes containing all combinations of alkyl, halogen, hydrogen, and other organic groups. As an example, the direct reaction of methyl chloride with silicon can produce a wide range of silane materials, for example, silane, trichlorosilane, tetrachlorosilane, tetramethylsilane, methytrichlorosilane, dimethyldichlorosilane, trimethylchlorosilane, methyldichlorosilane, and dimethylchlorosilane.

In the modern manufacture of silicones, diorganodihalosilanes, dimethyldichlorosilane in particular, constitute the bulk of the silane intermediates that are processed to produce the siloxane intermediates that are utilized in most silicone products. When one considers that hundreds of millions of pounds of silanes are produced annually worldwide to support the commercial manufacturing of silicones, it can be appreciated that even small increments of improvement in selectivity in crude product distribution and of improvement in raw material efficiency have a significant impact upon these manufacturers. As an example, assuming a manufacturer produces ten million pounds of dimethyldichlorosilane annually, a two to four weight percent reduction in the silicon raw material requirement would have a significant economic impact and would be quite attractive to the manufacturer.

For the purposes of the instant invention, the efficiency of utilizing raw materials is tracked by the amount of silicon charged that is converted to silanes. This conversion of silicon to silanes will be hereafter denoted as "% Si conversion". Those skilled in the art are interested in the selectivity of the direct reaction, particularly the formation of diorganodihalosilanes compared to less preferred organohalosilanes and halosilanes. In the preparation of methylchlorosilanes, a measure of selectivity of particular intereat is the ratio of methyltrichlorosilane (Me) to dimethyldichlorosilane (Me$_2$). For the purposes of the instant invention, this measure of selectivity will be denoted by the ratio "Me/Me$_2$". In the literature, this ratio is often referred to as "M/M$_2$" or "T/D". Therefore, an increase in the Me/Me$_2$ ratio indicates that there is an decrease in the output of the more preferred dimethyldichlorosilane, Conversely, a decrease in the ratio indicates that there is an increase in the output of the more preferred dimethyldichlorosilane.

Rochow, U.S. Pat. No. 2,380,995, issued Aug. 7, 1945, showed contacting methyl chloride vapor with silicon at about 300° C. yielded a silane mixture that was predominantly methyltrichlorosilane and dimethyldichlorosilane at 52 and 14,5 weight percent, respectively. This results in a Me/Me$_2$ ratio of 3.6. Rochow also discloses the use of a 50/50 weight silicon-copper alloy and the use of metallic catalysts other than copper, such as nickel, tin, antimony, manganese, silver, and titanium. The physical forms and the amounts of these catalysts are not disclosed by Rochow.

Rochow and Patnode, U.S. Pat. No. 2,380,996, issued Aug, 7, 1945, and Patnode, U.S. Pat. No. 2,380,997, issued Aug, 7, 1945, disclose the preparation of a contact mass for the direct reaction, the method comprising the subjecting of a mixture of silicon, copper, or other metallic catalysts to a reducing atmosphere during firing. Rochow and Patnode and Patnode also disclose the use of nickel, tin, antimony, manganese, silver, and titanium.

Rochow and Gilliam, U.S. Pat. No. 2,383,818, issued Aug, 28, 1945, discloses the use of contact masses comprising silicon and an oxide of copper. Also, included are copper compounds which are readily converted to the oxides, such as copper nitrate. Overall yield and the Me/Me$_2$ ratio are not disclosed.

Ferguson and Sellers, U.S. Pat. No. 2,443,902, issued June 22, 1948, disclose an attempt to increase the yield of dialkyldihalosilanes from the direct reaction. Ferguson and Sellers discloses the reaction between an alkyl halide and silicon in the presence of a finely divided cupreous catalyst, having as a principal constituent, friable metallic copper core surrounded by protective surface films of cuprous oxide, inhibiting oxidation in air, said films being relatively thin compared with the size of the enclosed copper cores. Two examples showed that Me/Me$_2$ ratios of 0.18 and 0.77, respectively were obtained. For these two examples, the percent of silicon converted that was converted to dimethyldichlorosilane was 82.4 and 65.6, respectively.

Gilliam, U.S. Pat. No. 2,464,033, issued March 8, 1949 discloses the use of copper halides, in addition to copper metal and copper oxides, as catalysts in the direct process. Further, Gilliam discloses the use of "promoters" such as zinc, or zinc halides, or their mixtures. Favorable Me/Me$_2$ ratios in a range from about 0.20 to 0.40 were demonstrated. Corresponding figures on the percent of silicon converted that was converted to dimethyldichlorosilane were in a range from about 45 to 65.

Nitzsche, U.S. Pat. No. 2,666,775, issued Jan, 19, 1954, discloses the use of alloys of silicon with either copper or iron or both which were activated with chlorides. The results were a Me/Me$_2$ ratio of 0.90.

From an abstract published in *Chemical Abstracts*, 58 (1963), 13995, a method utilized by Golubstov et al., in a U.S.S.R. Patent publication, published Oct. 31, 1962, discloses the use of arsenic as an accelerator to increase the output of dimethylchlorosilane, $(CH_3)_2HSiCl$, from the reaction of a silicon-copper alloy with methyl chloride. No mention is made of the output of dimethyldichlorosilane. Further, Golubstov et al., does not disclose the combination of arsenic with copper or copper compounds, zinc or zinc compounds, and phosphorous or phosphorous compounds, as does the instant invention.

Rossmy, U.S. Pat. No. 3,069,452, issued Dec. 18, 1962, discloses the use of a brittle, grindable silicon-copper alloy as a catalyst for the direct reaction of silicon and an alkyl halide. The use of this new copper catalyst results in $Me/Me_2$ ratios as low as 0.13.

Lobusevich et al., *Zhurnal Obshchei Khimii*, (August, 1964), 34:8, pp. 2727-2729, discloses that arsenic at a concentration of 0.05 to 1.0 weight percent is a promoter in raising the total and selective activities of silicon-copper alloys in the direct reaction with methyl chloride to produce methylchlorosilanes, Lobusevich et al., in FIG. 4 summarizes the impact of arsenic when the direct reaction is run at a temperature of 320° C. Over the range of arsenic content studied, the content of dimethyldichlorosilane in the reaction product is increased from approximately 50 weight percent to approximately 65 weight percent. No mention is made of the $Me/Me_2$ ratio. Further, no mention is made of the percentage of silicon converted to dimethyldichlorosilane.

Rossmy, German Pat. No. 1,165,026, published March 12, 1964, discloses the use of silicon-copper alloys for the preparation of methylchlorosilanes. The silicon-copper alloys were prepared by sintering a finely ground silicon-copper with an additive such as phosphorous, arsenic, antimony, indium, thallium, and gallium in a stream of hydrogen at temperatures of about 1000° C. Example 3 of Rossmy outlines the use of arsenic as the additive to the silicon-copper alloy. More specifically, ferrosilicon containing 95.5 percent silicon was was sintered in a stream of hydrogen at 1030° C. with $Cu_3Si$ and arsenic, wherein the arsenic content was 0.09 weight percent or 900 parts per million (ppm). The resulting alloy was reacted with methyl chloride at 290° C. to yield a reaction product mixture containing 77.5 percent dimethyldichlorosilane and having a $Me/Me_2$ ratio of approximately 0.17. No mention is made of the percentage of silicon converted to methylchlorosilanes. Special note should be taken of the manner in which the arsenic was introduced into the reaction of the methyl chloride and the silicon-copper mass.

Zock, U.S. Pat. No. 3,446,829, issued May 27, 1969, discloses the use of a cadmium promoter with a copper or silver catalyst with silicon in the direct reaction. The advantages forwarded by Zock are increased rate of reaction; increased selectivity for the formation of dimethyldichlorosilane; and high silicon conversion rate.

U.S. Pat. No. 4,218,387, issued Aug. 19, 1980. discloses the preparation of catalytic copper in terms of its particle size and copper (I) oxide content to give higher yields and greater selectivity. Maas et al., shows an example of a $Me/Me_2$ ratio as low as 0.90. No mention is made of the percentage of silicon converted to methylchlorosilanes.

Downing et al., European Patent Application No. 0 028 009 A2, published, May 6, 1981, discloses a copper-catalyzed silicon reaction mass for the production of methylchlorosilanes which comprises free-flowing powders or particles of silicon metal having spots of copper-silicon alloy substantially uniformly distributed on the surface of the silicon particles. Zinc powder is optionally used in the reaction mass. Downing et al., provide only one example of the use of this reaction mass to produce methylchlorosilanes. A $Me/Me_2$ ratio of approximately 0.07 is reported by Downing et al. No reference is made to the percentage of silicon converted to dimethyldichlorosilane.

Ward et al., U.S. Pat. No. 4,487,950, issued Dec. 11, 1984, discloses the preparation of methylchlorosilanes from the direct reaction of methyl chloride and particulated silicon which has been contacted with a mixture of partially oxidized copper catalyst and copper formate. Ward et al., discloses a $Me/Me_2$ ratio as low as 0.09.

Ward et al., U.S. Pat. No. 4,500,724, issued Feb. 19,1985, discloses the use of tin as a co-catalyst with copper and zinc, especially when copper is in the form of copper chloride. Ward et al., claim that the reaction rate and the selectivity of the direct reaction of silicon with an alkyl halide are achieved when attention is paid to the critical weight percent of copper relative to silicon and the critical weight ratios of tin and zinc are employed relative to copper. Ward et al., in Table 1 of Example 1 summarizes the impact of tin upon the $Me/Me_2$ ratio. Ward et al., demonstrate that tin is needed, in combination with copper and zinc to minimize the $Me/Me_2$ ratio.

Hashiguchi, U.S. Pat. No. 4,503,165, issued March 5, 1985, discloses the use of hydroxides of Period IV metals, having atomic numbers between 24 and 30, as catalysts in conjunction with ground cupreous particulates in the preparation of alkyl and arylhalosilanes. Shoepe and Hashiguchi, U.S. Pat. No. 4,504,596, issued March 12, 1985, discloses the use of hydrated refractory oxides, such as hydrated alumina, with a major portion of cuprous and cupric oxides and a minor portion of copper in the preparation of alkyl and arylhalosilanes.

Prud'Homme European Patent Publication No. 0,138,678 A2, published Apr. 24, 1985, discloses a process for improving dimethylchlorosilane selectivity and maximum silicon conversion, the process comprising the reacting of a solid contact mass of silicon and a catalyst including copper or a copper compound with the catalyst additionally including tin or antimony or compounds of tin or antimony and cesium or a cesium compound. Prud'Homme also discloses that zinc or zinc compounds may also be included in the catalyst, and further that zinc may be partially replaced by another metal such as aluminum, cadmium, manganese, nickel, or silver. Prud'Homme discloses that it is necessary for either tin or antimony to be present in the catalyst for the beneficial effects of the invention to be obtained. Prud'Homme further discloses that high selectivity can be obtained whenever the catalyst is used at a temperature of 330-350° C. Prud'Homme presents 9 examples applying the catalyst of the invention in which $Me/Me_2$ ratios ranging from 0.04 to 0.08 and silicon conversions ranging from 74 to 89 percent ar reported. In a comparative example in which tin or antimony is not present the $Me/Me_2$ ratio is 0.08 and a silicon conversion of 4 percent. Thus tin or antimony must be present to have both high selectivity and high silicon conversion Prud'homme, European Patent Publication No. 0 138 679, published Apr. 24, 1985, makes a similar disclosure in which lithium, sodium, potassium, and rubidium metal and compounds of these metals are utilized with tin or antimony. Me/Me₂ ratios ranging from approximately 0.09 to 0.13 are reported Prud'homme, European Patent Publication No, 0 194 214, published Sept, 10, 1986, makes a similar disclosure in which beryllium, magnesium, and calcium metal and compounds of these metals are utilized with tin or antimony. A Me/Me$_2$ ratio of 0.09 is reported.

Prud'Homme, U.S. Pat. No. 4,645,851, issued Feb, 24, 1987, discloses as similar invention in which barium or strontium are added as metals or compounds thereof, in place of cesium or cesium compounds, When the catalyst of the invention was applied, results reported showed Me/Me$_2$ ratios ranging from 0.05 to 0.10 and silicon conversions ranging from 52 to 70 percent. When the catalyst was applied without tin the Me/Me$_2$ ratio was 0.19 and the silicon conversion was not reported.

Ritzer et al., United Kingdom Patent Application GB No, 2,153,697, published Aug, 29, 1985, discloses catalysts for the production of organohalosilanes comprising copper and copper oxides, tin or tin-containing compounds, and aluminum or aluminum-containing compounds. Me/Me$_2$ ratios ranging from approximately 0.09 to 0.10 and silicon conversion ranging from about 28 to 45 percent were reported.

Halm et al., U.S. Pat. No. 4,602,101, issued July 22, 1986, discloses a method for controlling a process for the manufacture of alkylhalosilanes, said process comprising contacting an alkyl halide with metallurgical grade silicon, at a temperature of 250–350° C., in the presence of tin or tin compounds, and copper or copper compounds, wherein there is present as a promoter phosphorous or phosphorous-containing compounds. The benefits of the invention of Halm et al., are increased halosilane yields, increased selectivity of dialkyldihalosilanes over other, less preferred alkylhalosilanes, and overall higher utilization of raw materials. Me/Me$_2$ ratios as low as 0.04 and silicon conversions as high as 87 percent were reported. As in most of the above references, tin is a necessary component of the catalyst to realize the benefits of the invention of Halm et al.

Lewis and Childress, European Patent Publication No, 0 191 502 A2, published Aug, 20, 1986, discloses an improved direct process wherein the tin and zinc promoter content in the catalyst are controlled at a promoter to tin ratio of 10 to 250, by weight, Me/Me$_2$ ratios down to as low as 0.035 were reported. However silicon conversion was very low, normally less than 20 percent.

None of the above references show that a low Me/Me$_2$ ratio can be attained with high conversion of silicon to methylchlorosilanes without the use of tin or antimony in the contact mass for the direct reaction. Further, none of the above references have shown that arsenic or compounds of arsenic when added to the direct reaction of silicon and methyl chloride will allow the minimum Me/Me$_2$ ratio and maximum silicon conversion to methylchlorosilanes that is obtained when tin or tin compounds are used in the direct reaction.

SUMMARY OF THE INVENTION

The inventors herein have found that arsenic or arsenic compounds when use as described, infra, give enhanced overall yields, increased selectivity towards the formation of dimethyldichlorosilane, and the benefit of increased utilization of the raw materials in the direct reaction for manufacturing alkylhalosilanes.

It has been unexpectedly found that arsenic or arsenic compounds can be directly used as a replacement for tin or tin compounds as a catalyst in the direct reaction of an alkyl halide with silicon to produce alkylhalosilanes to yield both high selectivity toward the desired dialkyldihalosilane and high conversion of silicon to organohalosilanes.

DESCRIPTION OF THE INVENTION

In accordance with the instant invention, there is provided a method for controlling a process for the manufacture of alkylhalosilanes under conditions that will be delineated herein. What is described, therefore, is a method for controlling a process for the manufacture of alkylhalosilanes, said method comprising contacting an alkyl halide with metallurgical grade silicon at a temperature in a range from about 250° to 350° C., said silicon being in a contact mass in the presence of zinc or zinc compounds, copper or copper compounds, and phosphorous or phosphorous compounds and in the absence of tin or tin compounds, wherein the zinc or zinc compounds are present in an amount such that the zinc content of the contact mass is in a range from about 100 to 10,000 parts per million by weight; wherein the copper or copper compounds are present in an amount such that the copper content of the contact mass is in a range from 0.2 to 10 weight percent, wherein the phosphorous or phosphorous compounds are present in an amount such that the phosphorous content of the contact mass is in a range from about 25 to 2500 parts per million by weight, and wherein there is at least also present in the contact mass greater than about 50 parts per million by weight arsenic, wherein the arsenic is introduced as arsenic metal, a metal arsenide or a metal alloy of arsenic.

For the purposes of the instant invention the term "contact mass" means the mixture of silicon and other solids, catalysts and promoters used to facilitate the reaction of an alkyl halide and silicon to produce alkylhalosilanes.

It has been found that the process herein can be any of those, described supra, in which the direct reaction as disclosed by Rochow in U.S. Pat. No. 2,380,995, uses silicon and copper as long as there is also present phosphorous and zinc, in some form and arsenic, metal arsenides or metal alloys of arsenic, in the absence of tin or tin compounds, as set forth hereinafter.

For example, the process can be that which is disclosed in Rochow and Gilliam, U.S. Pat. No. 2,383,818, so long as there is also present zinc and phosphorous and an absence of tin, as disclosed herein. The process can, for example, be that set forth in Ferguson and Sellers, U.S. Pat. No. 2,443,092; or that set forth in Gilliam, U.S. Pat. No. 2,464,033, using copper halides or oxides; or that set forth by Gilliam also including zinc to give silicon, copper, and zinc in combination; or that process set forth in Maas, U.S. Pat. No. 4,218,387; or that set forth in Ward et al., U.S. Pat. No. 4,487,950, using copper formate; or that process set forth in Ward et al., U.S. Pat. No. 4,500,724, as long as there is also zinc and phosphorous or compounds thereof, in the absence of tin or tin compounds as described in the instant invention; such processes and the disclosures associated therewith being incorporated herein by reference.

Thus, what is disclosed as the invention herein is a method for controlling a process for making alkylhalosilanes by contacting alkyl halides with silicon in the presence of copper, zinc, phosphorous, and arsenic, or compounds thereof, wherein the arsenic is described, infra.

The benefits to be derived by the use of the instant invention are enhanced overall yield; enhanced selectivity in favor of dialkyldihalosilanes; and increased conversion of raw materials into usable products. These benefits are derived by the replacement of tin as a promoter for the direct reaction with arsenic or arsenic compounds.

The alkylhalosilanes of the instant invention are those having the general formula (I) $R_nSiX_{4-n}$ and (II) $R_mH_qSiX_{4-m-q}$ with the former silanes being the preferred silanes of the invention. In the above formulae, each R is independently selected from alkyl groups having 1 to 4 carbon atoms, n has a value of 1, 2, or 3, m has a value of 1 or 2, q has a value of 1 or 2, and the sum of m+q cannot be greater than 3, and X is a halogen atom. Preferred silanes are those having the formula, $R_2SiX_2$ and $R_3SiX$, wherein R is methyl or ethyl and X is chlorine. Most preferred is the silane, $(CH_3)_2SiCl_2$.

Although methyl chloride is the preferred alkyl halide for this invention, other alkyl halides can be, for example, ethyl chloride, n-propyl chloride, and isopropyl chloride.

The silicon useful in the instant invention is any silicon having a purity of at least g5 percent by weight (wt %) but less than 100 wt. % silicon. An example of such silicon is metallurgical-grade silicon. The silicon for the purposes of the instant invention can be particulated silicon or it can be particulated silicon/copper, whether in the form of discrete copper and discrete silicon particles or it can be a silicon/copper alloy which has been particulated.

The silicon or silicon/copper is fed into an appropriate reactor as needed. This process can be carried out under continuous conditions in a fluid bed, in a stirred bed, or fixed bed reactor or in a batch mode, wherein the beds can be vibrated or not, depending upon the desired results. Preferred are the continuous modes of operation. Most preferred is a continuous fluid bed reactor.

The alkyl halide, or an inert gas such as argon, nitrogen, or mixtures thereof can be utilized to fluidize the bed of particles in the reactor. The particle-size distribution of the solids of the reaction or contact mass should be a particle-size distribution known in the art to be suitable for a fluid bed reactor. For example, Dotson in U.S. Pat. No. 3,133,109, discloses that for optimum results in the direct reaction of methyl chloride with silicon the particles in a fluidized bed should have an average particle size of from about 20 to 200 microns. As a further example, Ward et al,, in U.S. Pat. No. 4,500,724, issued Feb. 19, 1985, disclose that silicon present in a fluidized bed can have a particle size below 700 microns; with an average particle size greater than 20 microns and less than 300 microns; preferably with a mean diameter of 100 to 150 microns.

Thus, the particles in the reactor can have an average particle size ranging from 0.1 to 800 microns, it being preferred to use particles having an average particle size of 0.1 to 150 microns. It is understood that this preferred range of average particle sizes is chosen to cover the various scale of fluid bed reactor, each scale possibly requiring a different particle size distribution.

The process of the instant invention can be carried out in a temperature range from about 250° to 350° C.
and it is preferred that the process be carried out in a range of 260° to 330° C. Most preferred is a temperature range of 280° to 320° C.

Generally, the components and reactants of the system, with the exception of the alkyl halide, are blended together in the reactor and heated to the reaction temperature and held for a short period of time. The alkyl halide, with or without the assistance of an inert gas, is fed into the reactor and the gaseous reaction products and the gaseous unreacted alkyl halide are passed through and removed from the reactor. The unreacted alkyl halide and the reaction products are condensed and recovered and then separated by distillation. Any particulate material flowing through the reactor is also trapped and removed either to be recycled to the reactor or discarded.

It is within the scope of the instant invention to utilize the apparatus of Dotson, U.S. Pat. No. 3,133,109, among others, to carry out the process of the instant invention, it being understood that the apparatus can be used as described by Dotson or it can be further modified by those skilled in the art to assist in the optimum selectivity and maximum amount of alkylhalosilane obtainable. It should also be understood that purified alkyl halides are preferred for the inventive process, but are not required. It should be further understood and appreciated that the treatment of silicon particles, as set forth by Shade in U.S. Pat. No. 4,281,149, and the improvement disclosed by Shah et al., in U.S. Pat. No. 4,307,242, can be effectively used herein.

The inventors have found that arsenic is a suitable replacement for tin, in combination with zinc and phosphorous, in the direct reaction to maximize selectivity and conversion of silicon to organohalosilanes. The inventors have also found that tin added in addition to arsenic is detrimental to the maximization of the Me/Me$_2$ ratio. Thus, the instant invention requires that tin be absent. Thus, aside from the silicon and copper required in the direct reaction, there is required by this invention, the presence of arsenic, zinc, and phosphorous and the absence of tin.

Arsenic, which is critical to the instant invention as a promoter, is arsenic metal, metal arsenides, and metal alloys of arsenic. Metal arsenides can be, for example, copper arsenide, $Cu_3As$; calcium arsenide, $Ca_3As_2$; iron arsenide, $FeAs_2$; or zinc arsenide, $Zn_3As_2$. Metal alloys of arsenic can be, for example, arsenical copper (30 weight percent arsenic in copper) or aluminum/arsenic alloys.

The amount of arsenic promoter useful herein is greater than about 50 parts per million (ppm), calculated as arsenic and based upon the weight of solids—silicon, copper or copper compounds, zinc or zinc compounds, and phosphorous or phosphorous compounds—charged to the reactor. The preferred amount of arsenic promoter is in a range from about 100 to 500 ppm arsenic, based upon the weight of the solids charged to the reactor.

The phosphorous may be, for example, elemental phosphorous such as red phosphorous, metal phosphides, and phosphorous compounds which are capable of forming metal phosphides, The zinc may be, for example, zinc metal, alloys of zinc metal such as brass alkylzinc compounds, zinc oxide, and zinc halides.

The amounts of phosphorous and zinc normally used in catalysts for the direct reaction are those amounts intended for use herein. Thus, from about 25 to 2500 ppm phosphorous, based upon the weight of the solids fed to a reactor can be used herein without significantly detracting from the invention as described. Likewise, from about 100 to 10,000 ppm zinc, based upon the weight of the solids fed to a reactor can be used herein without significantly detracting from the invention as described.

The arsenic, phosphorous, and zinc, along with silicon and copper and any other desirable materials can be introduced to the reactor as a contact mass by introducing the components separately or as a mixture, masterbatch, alloy, or blend of two or more of the various components.

In accordance with the instant invention there is also provided a composition useful in the direct reaction. What is described, therefore, is a composition of matter comprising metallurgical grade silicon; zinc or zinc compounds present in such an amount that zinc content of the composition is in a range from about 100 to 10,000 parts per million by weight; copper or copper compounds present in such an amount that copper content of the composition is in a range from about 0.2 to 10 weight percent; phosphorous or phosphorous compounds present in such an amount that phosphorous content of the composition is in a range from about 25 to 2500 parts per million by weight; and an arsenic promoter present in such an amount that the arsenic content of the composition is greater than about 100 parts per million by weight.

Aside from the silicon in the composition, there is present from about 0.2 to 10 weight percent copper, from about 100 to 10,000 ppm zinc as zinc, from about 25 to 2500 ppm phosphorous as phosphorous; and from about 100 ppm arsenic as arsenic, all weights and parts being based upon the total weight of the composition.

Arsenic, which is critical to the instant invention as a promoter, is arsenic metal, metal arsenides, and metal alloys of arsenic. Examples of metal arsenids and metal alloys of arsenic are discussed, supra.

Zinc or zinc compounds, copper or copper compounds, and phosphorous or phosphorous compounds are discussed, supra.

In addition, it is also beneficial that the compositions include aluminum and iron. Therefore, there can be present in the composition from about 200 to 10,000 ppm aluminum and up to about 1 percent iron, all proportions being based upon the total weight of the composition. Whenever the quantities of these ingredients are referred to herein, the quantities are based upon the metal actually present in the composition. The composition can be mixtures of all such ingredients or mixtures of only some of the ingredients, so long as the composition contains the required silicon, copper, zinc, phosphorous, and arsenic.

So that those skilled in the art may better understand and appreciate the instant invention, the following examples are presented. These examples are presented as being illustrative and are not to be construed as limiting the invention as claimed herein.

EXAMPLE 1

(Not Within The Scope Of The Instant Invention)

The equipment, procedures analytical techniques, and notation utilized in this example will be used in the subsequent examples.

The reactor used for these examples is similar to that described in Maas et al., U.S. Pat. No. 4,218,387, and is familiar to those skilled in the art of producing methylchlorosilanes using silicon and methyl chloride. In general, the reaction is carried out by passing the methyl chloride, in vapor or gaseous form, over the surface of the silicon charge at an elevated temperature. The heating of the reactant mixture is carried out, in this case, by immersing the reactor in a sand bath as a heat transfer medium.

The products of the reaction and any unreacted materials are condensed and collected in cold traps immersed in a bath of dry ice and isopropanol. The products and unreacted materials are evaluated by gas chromatography by pouring the collected materials into bottles cooled with dry ice/isopropanol, cooling the chromatograph syringe and injecting samples into the gas chromatograph as quickly as possible.

The charge to the reactor is prepared by grinding silicon and shaking the ground silicon in a bottle for two or three minutes with any other solid ingredients desired to be included in the reaction. The charge is placed in the reactor and the reactor is closed and weighed to give initial charge weights. The gas flow for fluidization is started. The reactor is immersed in the sand bath. The receivers for the effluent are also weighed and the connected by tubes to the reactor. The reactor is heated by the sand bath and the bath is continuously fluidized to maintain close tolerances on the temperature.

The receiver (cold traps) are placed in the dry ice baths. After a few minutes the methyl chloride flow to the reactor is started. After certain periods of time and at varying temperatures which are described in detail below, the methyl chloride flow is terminated, and the receivers are disconnected and weighed prior to analysis. The reactor is removed from the sand bath after cooling and it is also weighed.

For purposes of interpreting the results of these examples, the following apply:

$$\text{Me/Me}_2 \text{ ratio} = \frac{\text{Weight \% Methyltrichlorosilane}}{\text{Weight \% Dimethyldichlorosilane}} \quad 1.$$

$$\text{Percent Silicon Conversion} = \% \text{ Si Conversion} = \quad 2.$$

$$100 - \frac{\text{Weight silicon left}}{\text{Weight silicon charged}} \times 100$$

A run was made without the use of arsenic or an arsenic compound and without tin or a compound of tin as a catalyst in the reaction contact mass.

Metallurgical grade silicon, wherein 85 weight percent of the silicon has a particle size less than 70 microns was utilized. The reaction contact mass further included:

| | |
|---|---|
| 6.1 weight percent | Cu$_2$Cl$_2$ |
| 600 ppm | Brass |
| 2000 ppm | 15% P in Cu Alloy |

The silicon was Globe Metallurgical Grade Silicon available from Globe Metallurgical, Inc., Cleveland, Ohio, and contains the following impurities, the impurities being reported as ppm by weight:

| Compound | Amount (ppm) |
|---|---|
| Iron | 5000 |
| Aluminum | 3300 |
| Calcium | 720 |
| Titanium | 380 |
| Vanadium | 110 |

-continued

| Compound | Amount (ppm) |
| --- | --- |
| Nickel | 70 |

The $Cu_2Cl_2$ was purchased from Calabrain Chemicals Corporation, Houston, Tex. The 15% P in Cu alloy was purchased from Greenback Industries, Greenback Tenn. The brass had a zinc composition of 50 weight percent.

The reactor was placed in a sand bath at 315° C. Methyl chloride was then fed to the reactor. The reaction was continued for about 44 hours with all the products and unreacted materials being collected in the cold traps. Sampling and the results reported are at the end of the 44-hour reaction time.

Table 1 is a summary of the results of this run. This run is designated as Sample A. The results reported are: (a) weight percent dimethyldichlorosilane in the crude product, designated as "%Me$_2$"; the Me/Me$_2$ ratio, designated as "Me/Me$_2$"; and percent silicon conversion to methylchlorosilanes designated as "%Si Conv".

TABLE 1

| Sample | % Me$_2$ | Me/Me$_2$ | % Si Conv |
| --- | --- | --- | --- |
| A | 76.5 | 0.16 | 15.4 |

The above results demonstrate that in the absence of arsenic or tin, high selectivity is not achieved and silicon conversion to organohalosilanes is low.

EXAMPLE 2

(Not Within The Scope Of The Instant Invention)

A run was made using the apparatus, procedures, and many of the raw materials Example 1. The components of the reaction contact mass were:

| 6.1 weight percent | $Cu_2Cl_2$ |
| --- | --- |
| 2000 ppm | 15% P in Cu Alloy |
| 30 ppm | Tin |

Table 2 is a summary of the average results of this series of runs. The notation used is the same as that used in Example 1. This series of runs is designated Sample B.

TABLE 2

| Sample | % Me$_2$ | Me/Me$_2$ | % Si Conv |
| --- | --- | --- | --- |
| B | 76.2 | 0.15 | 75.8 |

The above results demonstrate the level of selectivity and silicon conversion to organohalosilanes that is attained when the direct reaction is catalyzed with copper, phosphorous, and tin.

EXAMPLE 3

(Not Within The Scope Of The Instant Invention)

A series of 90 runs was made using the apparatus, procedures, the silicon from Example 1 and the following other components of the reaction contact mass:

| 6.1 weight percent | $Cu_2Cl_2$ |
| --- | --- |
| 600 ppm | Brass |
| 30 ppm | Tin |

Table 3 is a summary of the average results of this series of runs. The same notation as used in Example 1 are used. This series of runs is designated Sample C.

TABLE 3

| Sample | % Me$_2$ | Me/Me$_2$ | % Si Conv |
| --- | --- | --- | --- |
| C | 83.6 | 0.09 | 73.5 |

The above results demonstrate the level of selectivity and silicon conversion to organohalosilanes that is attained when the direct reaction is catalyzed with copper, zinc, and tin.

EXAMPLE (Not With The Scope Of The Instant Invention)

A series of 42 runs was made using the apparatus, the procedures, the silicon from Example 1 and the following other components of the reaction contact mass:

| 6.5 weight percent | $Cu_2Cl_2$ |
| --- | --- |
| 600 ppm | Brass |
| 30 ppm | Tin |
| 2000 ppm | 15% P in Cu Alloy |

Table 4 is a summary of the average results of this series of runs. The same notation as used in Example 1 apply. This series of runs is designated Sample D.

TABLE 4

| Sample | % Me$_2$ | Me/Me$_2$ | % Si Conv |
| --- | --- | --- | --- |
| D | 90.5 | 0.05 | 71.4 |

The above results demonstrate the high selectivity and silicon conversion achieved when tin is used as a catalys. along with copper, phosphorous and zinc,

EXAMPLE 5

A series of runs was made in which an arsenic-copper powder was added to the reaction contact mass in place of tin. The apparatus, procedures and many of the raw materials are the same as used in Example 1. In addition to silicon, the reaction contact mass consisted of the following components:

| 6.1 weight percent | $Cu_2Cl_2$ |
| --- | --- |
| 600 ppm | Brass |
| 2000 ppm | 15% P in Cu Alloy |
| 100 to 1000 ppm | Arsenic—Copper Alloy |

The arsenic-copper alloy was 30 weight percent arsenic purchased from Metallurgical Products Company, West Chester, Pa. Therefore, the arsenic content of the reaction contact mass ranged from about 30 to 300 ppm arsenic, Four runs were made at varying levels of arsenic—30, 75, 150, and 300 ppm arsenic—these four runs being designated Sample E, F, G, and H, respectively. Table 5 is a summary of the results of these runs. The notation used in Example 1 are used herein. Arsenic content is designated in Table 5 as "ppm As".

TABLE 5

| Sample | ppm As | % Me$_2$ | Me/Me$_2$ | % Si Conv |
|---|---|---|---|---|
| E | 30 | 67.5 | 0.20 | 38.0 |
| F | 75 | 73.8 | 0.16 | 46.9 |
| G | 150 | 88.3 | 0.07 | 78.8 |
| H | 300 | 85.7 | 0.09 | 61.0 |

The above results demonstrate the impact that the use of a copper-arsenic alloy in the direct reaction has upon selectivity and silicon conversion when used in place of tin.

EXAMPLE 6

A run was made in which copper arsenide (Cu$_3$As) was added to the reaction contact mass in place of tin. The apparatus, procedures and many of the raw materials are the same as used in Example 1. In addition to silicon, the reaction contact mass consisted of the following components:

| | |
|---|---|
| 6.1 weight percent | Cu$_2$Cl$_2$ |
| 600 ppm | Brass |
| 2000 ppm | 15% P in Cu Alloy |
| 500 ppm | Cu$_3$As |

Cu$_3$As is 28.2 weight percent arsenic purchased from CERAC, Inc., CERAC/PURE Division, Milwaukee, Wis. Therefore, the arsenic content of the reaction contact mass is about 140 ppm arsenic. The run is designated Sample J. Table 6 is a summary of the results of these runs. The notation used in Example 1 are used herein. Arsenic content is designated in Table 6 as "ppm As".

TABLE 6

| Sample | ppm As | % Me$_2$ | Me/Me$_2$ | % Si Conv |
|---|---|---|---|---|
| J | 140 | 88.1 | 0.07 | 82.8 |

The above results demonstrate the impact that the use of a metal arsenide in the direct reaction has upon selectivity and silicon conversion when used in place of tin.

EXAMPLE 7

(Not Within The Scope Of The Instant Invention)

A run was made in which both an arsenic-copper powder and tin were added to the reaction contact mass. The apparatus, procedures and many of the raw materials are the same as used in Example 1. In addition to silicon, the reaction contact mass consisted of the following components:

| | |
|---|---|
| 6.1 weight percent | Cu$_2$Cl$_2$ |
| 600 ppm | Brass |
| 2000 ppm | 15% P in Cu Alloy |
| 1000 ppm | Arsenic—Copper Alloy |
| 30 ppm | Tin |

The arsenic-copper alloy was 30 weight percent arsenic purchased from Metallurgical Product Company, West Chester, Pa. Therefore, the arsenic content of the reaction contact mass was 300 ppm arsenic. Table 7 is a summary of the results of this run. The notation used in Example 1 is used herein. Arsenic content is designated in Table 7 as "ppm As". The run is designated as Sample K.

TABLE 7

| Sample | ppm As | % Me$_2$ | Me/Me$_2$ | % Si Conv |
|---|---|---|---|---|
| K | 300 | 79.1 | 0.14 | 77.6 |

The above results demonstrate that the combination of tin and arsenic do not appear to have the beneficial effect upon the selectivity of the direct reaction to produce organohalosilanes that might be expected.

What is claimed is:

1. A method for controlling a process for the manufacture of alkylhalosilanes, said method comprising contacting an alkyl halide with metallurgical grade silicon at a temperature in a range from about 250° to 350° C., said silicon being in a contact mass in the presence of zinc or zinc compounds, copper or copper compounds and phosphorous or phosphorous compounds and in the absence of tin or tin compounds, wherein the zinc or zinc compounds are present in an amount such that the zinc content of the contact mass is in a range from about 100 to 10,000 parts per million by weight; wherein the copper or copper compounds are present in an amount such that the copper content of the contact mass is in a range from 0.2 to 10 weight percent, wherein the phosphorous or phosphorous compounds are present in an amount such that the phosphorous content of the contact mass is in a range from about 25 to 2500 parts per million by weight, and wherein there is at least also present in the contact mass greater than about 50 parts per million by weight arsenic, wherein the arsenic is introduced as arsenic metal, a metal arsenide or a metal alloy of arsenic.

2. A method according to claim 1, wherein the arsenic is introduced as a metal arsenide.

3. A method according to claim 2, wherein the metal arsenide is copper arsenide.

4. A method according to claim 1, wherein the arsenic is introduced as a metal alloy of arsenic.

5. A method according to claim 4, wherein the metal alloy of arsenic is a copper-arsenic alloy.

6. A method according to claim 1, wherein the alkylhalosilanes are methylchlorosilanes and the alkyl halide is methyl chloride.

7. A method according to claim 1, wherein the process is carried out in a continuous mode.

8. A method according to claim 7, wherein the process is carried out in a fixed bed reactor.

9. A method according to claim 7, wherein the process is carried out in a fluid bed reactor.

10. A method according to claim 7, wherein the process is carried out in a vibrating bed reactor.

11. A method according to claim 7, wherein the process is carried out in a stirred bed reactor.

12. A method according to claim 1, wherein the process is carried out in a batch mode.

13. A method according to claim 1, wherein there is also present aluminum.

14. A method according to claim 13, wherein there is also present iron.

15. A composition of matter comprising metallurgical grade silicon; zinc or zinc compounds present in such an amount that zinc content of the composition is in a range from about 100 to 10,000 parts per million by weight; copper or copper compounds present in such an amount that copper content of the composition is in a range from about 0.2 to 10 weight percent; phosphorous or phosphorous compounds present in such an amount that phosphorous content of the composition is in a range from about 25 to 2500 parts per million by weight; and an arsenic promoter present in such an amount that the arsenic content of the composition is greater than about 100 parts per million by weight.

16. A composition of matter according to claim 15, wherein the promoter is a metal arsenide.

17. A composition of matter according to claim 15, wherein the promoter is a metal alloy of arsenic.

18. A composition of matter according to claim 15, wherein there is also present from about 200 to 10,000 parts per million by weight aluminum as aluminum, based upon the weight of silicon in the composition.

19. A composition of matter according to claim 18, wherein there is also present up to 1 weight percent iron as iron, based upon the weight of silicon in the composition.

* * * * *

UNITED STATES PATENT AND TRADEMARK OFFICE
CERTIFICATE OF CORRECTION

PATENT NO. : U.S. 4,762,940

DATED : August 9, 1988

INVENTOR(S) : Roland L. Halm, Andrew B. Pierce, and Oliver K. Wilding, Jr.

It is certified that error appears in the above-identified patent and that said Letters Patent is hereby corrected as shown below:

In the specification, Column 1, line 29, delete "1940'''" and insert therefor -- 1940's --.

Column 3, line 43, delete "900" and insert therefor -- 900 --.

Column 4, line 59, delete "ar" and insert therefor -- are --.

Column 7, line 28, delete "g5" and insert therefor -- 95 --.

Column 8, line 52-53, delete "solid-s-silicon" and inert therefor -- solids - silicon --.

Column 9, line 31, delete "100" and insert therefor -- 100 --.

Column 9, line 33, delete "100" and insert therefor -- 100 --.

Signed and Sealed this

Eleventh Day of April, 1989

*Attest:*

DONALD J. QUIGG

*Attesting Officer*  *Commissioner of Patents and Trademarks*